United States Patent [19]

Miwa et al.

[11] Patent Number: 5,527,377
[45] Date of Patent: Jun. 18, 1996

[54] MANUFACTURING METHOD OF METAL OR ALLOY

[75] Inventors: Yosuke Miwa; Junichi Ohsako; Motohisa Miyafuji; Isao Hosokawa; Syuhei Mori, all of Shimonoseki, Japan

[73] Assignee: Kabushiki Kaisha Kobe Seiko Sho, Kobe, Japan

[21] Appl. No.: 354,848

[22] Filed: Dec. 9, 1994

[30] Foreign Application Priority Data

Oct. 5, 1994 [JP] Japan .................................. 6-241660

[51] Int. Cl.⁶ ........................................................ C22B 9/16
[52] U.S. Cl. ........................ 75/376; 148/509; 164/452; 324/226
[58] Field of Search ..................... 75/375, 376; 148/509; 324/691, 699, 226; 164/452

[56] References Cited

U.S. PATENT DOCUMENTS

3,793,717  2/1974  Degenkolb ................. 148/509
4,799,010  1/1989  Muller ........................ 324/240

*Primary Examiner*—Melvyn Andrews
*Attorney, Agent, or Firm*—Oblon, Spivak, McClelland, Maier & Neustadt

[57] ABSTRACT

Conductivity distribution on the cross section of metal or alloy is measured by an eddy current type conductivity meter and conductivity distribution contour map is prepared. Based on the pattern of this conductivity distribution contour map, heat history of an ingot and segregation of added element are analyzed and melting and/or casting conditions of metal or alloy are re-established. This method allows to carry out the testing and analysis within short time and quickly provides assessment results for re-establishment of melting and/or casting conditions. Thereby, metal or alloy ingots which may create poor quality products during the following steps can be eliminated; in particular, applying this method to a manufacturing of copper precipitation hardening alloy and the like, more sound ingots can be obtained and suitability of ingots for the material which should be worked in the following step can be assessed.

6 Claims, 9 Drawing Sheets

MANUFACTURING METHOD OF METAL OR ALLOY

BACKGROUND OF THE INVENTION

1. Field of Invention

The present invention relates to a manufacturing method of metal or alloy wherein the conductivity map of the ingot are measured and the values obtained are fed back to establish the manufacturing conditions in the next step of metal or alloy manufacturing process, particularly relates to a manufacturing method suitable for manufacturing of precipitation hardening copper alloy.

2. Prior Art

Metal products are manufactured, for example, by mixing raw materials such as a main raw material, additives and the like first, melting these raw materials, casting the molten metal to obtain the ingots, then working said ingots by rolling and pressing and so on. Since the quality of ingots significantly effects on the quality of the finished product, it is necessary to increase the quality of the ingots first. For this purpose, the quality of the ingots must be determined in the manufacturing steps, and either or both melting and casting conditions must be controlled based on the results obtained.

Conventionally, the quality assessment of the ingots has been made based on the results obtained from testings such as the high-temperature tensile test, the high-temperature impact test, the observations of the macro- and microstructures of cross section of the ingot, the defect inspections including the liquid penetrant test and UT (ultrasonic) flaw detect and the like on some samples of the ingots.

However, in order to perform the quality assessment as mentioned above, after a part of the ingot must be cut out, the pieces of the ingot must be prepared into the predetermined shape for the test pieces and also a plurality of testings must be carried out. Therefore, it is time consuming and costs significantly.

Acceptability of working conditions at each step of the working process from the ingots to the finished product and the properties of the finished product only can be assessed at the time the working process has already proceeded to further step. Therefore, according to the prior art for the quality assessment of the ingots, it is difficult to reflect the results of the quality assessment of the ingots to the next step of the working process and to find and remove any poor quality product at the early step of the working process from the ingots to the finished product. If there is a part having a high residual stress locally in a ingot, this ingot may easily form cracks during the hot working process. Conventionally, however, because it takes time for measurement to obtain information such as distribution of residual stress and the like, the working process of the ingot proceeds before the test data are obtained. That is, when the quality assessment has completed, the ingot which should be considered to give a poor quality product by the working process thereafter to the finished product has already forwarded to the following step and therefore it is difficult to prevent a reduction of productivity and an increase of production cost due to generation of poor quality products.

In addition, non-destructive test using optical-induced image generation method is proposed (USP 510,112). According to this method, the subject of inspection is exposed to modulated heat source to induce a change of temperature in a part of the subject to be inspected. Local change of conductivity generated by this local change of temperature is detected by an eddy current probe and the detected change of conductivity is recorded to prepare a map of the response area of said probe. However, in the prior art there is no indication regarding application to the quality assessment of alloy ingot. This method itself, even if applied to alloy manufacturing method, does not allow a quick qualify assessment of ingot in the alloy manufacturing process.

SUMMARY OF THE INVENTION

The object of the present invention is to provide a manufacturing method of metal or alloy wherein melting and/or casting conditions to obtain complete casting materials can be easily and quickly obtained, these melting and/or casting conditions can be reflected to the following melting and/or casting process, any ingots having potential to produce a poor qualify products can be detected and removed, and thereby improvement of productivity and reduction of manufacturing cost can be realized.

The manufacturing method of metal or alloy according to the present invention comprises the steps of obtaining conductivity distribution pattern by determining conductivity on the surface or the cross section of a casting material and re-establishing the melting and/or casting conditions for raw materials based on this conductivity distribution pattern.

According to the manufacturing method of metal or alloy, the optimum melting and/or casting conditions can be obtained according to the composition and the like and the quality of ingots and the material characteristics after the working process can be predicted, because conductivity distribution pattern is obtained by determining conductivity on the surface or the cross section of a casting material, and the melting and/or casting conditions for raw materials are re-established based on this conductivity distribution pattern, Therefore, the present invention is very useful for improvement of productivity and effectiveness, and cost reduction of the product, because the melting and/or casting conditions can be changed quickly to the optimum conditions so that production of a poor quality product in the following steps is avoidable, and any products determined to be poor in quality can be removed at the early step of the working process so as to allow improvement of yield at the end of the rolling process and other working process.

DETAILED DESCRIPTION OF THE PREFERRED EMBODIMENTS

According to the present invention, conductivity on the surface or the cross section of metal or alloy casting material is determined and conductivity distribution pattern is prepared as a conductivity contour map, for example, by linking each point to point having the same conductivity by a curved line. Conductivity of a casting material changes according to the state of solid solution of added elements. In precipitation hardening alloy such as Cu-Fe alloy and the like, for example, the limit of solid solution of the added elements in relation to the main component is wider at higher temperature region and becomes narrower according to decrease of temperature. In such alloy, the amount of solid solution and precipitation of the added element is determined by the solidification temperature or cooling rate after heat treatment of the ingot. That is, if the ingot is cooled down faster than certain limitation, reduction of solid solution amount can not follow the rate of cooling so that the proportion of solid solution amount of added element in the alloy is high; that is, faster the cooling rate, higher the solid solution amount of added element.

On the other hand, solid solution amount of added element significantly effects on conductivity of the casting alloy; there is a relationship that conductivity of alloy becomes lower according to increase of solid solution amount of added element and higher according to decrease of solid solution amount of added element. Therefore, if conductivity is determined at each point on the surface or the cross section of the ingot and if distribution pattern of conductivity is shown as a two-dimensional or three-dimensional conductivity contour map, heat history, segregation status of the added element, distribution of impurities and the like of that casting material can be easily analyzed based on the conductivity contour map. Further, said conductivity determination does not require any complicate sample preparation and the like so that these analyses can be completed within a short time.

Figure 1:
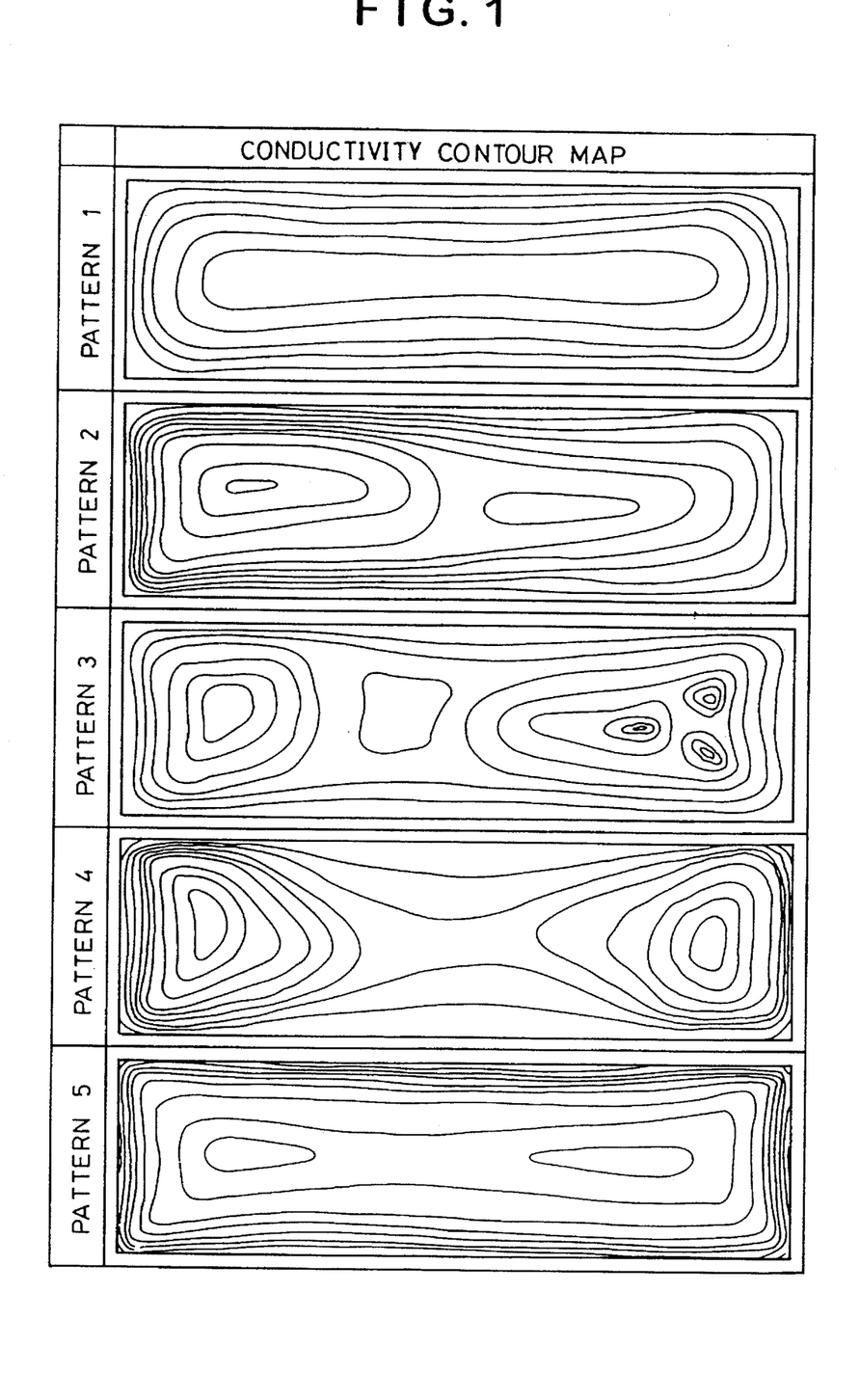
FIG. 1 is one example of conductivity contour maps.

FIG. 1 is one example of conductivity contour map showing conductivity distribution pattern on the cross section of an ingot. As shown in the pattern 1, conductivity is lower at the edge and higher at the center part of the cross section of the ingot, each conductivity contour is placed at almost same interval and does not form small enclosed zone. In this case, it can be judged that casting conditions were appropriate.

As shown in the pattern 2, in case contour is asymmetric and the gradient of conductivity (referred thereafter as to "the gradient") is larger at either right or left side of the ingot and there are small enclosed zones, it can be judged that temperature distribution of the mold was not uniform because flow rate of either the primary or secondary cooling water was different at right and left sides of the mold, or molten metal flowed from left to right of this pattern due to imbalance of the right and left molten metal distributors.

As shown in the pattern 3, in case small enclosed zones are located in either right or left side, it can be considered that there was disparity of cooling between both sides, or there occurred dynamic distortion of the mold during use thereof, or there occurred static distortion of the mold during repeated use thereof. It is also considered that there was the added element segregated and gas was occluded in the small enclosed zone.

As shown in the pattern 4, in case contour is constricted in the middle of the ingot, it can be judged that the primary cooling added to both sides of the ingot was excess so that the residual stress of the ingot was high at both sides. If the residual stress was locally high, cracks may occur during heating step of the hot rolling. It is also considered to create poor contact between the mold and the ingot shell because the shape of the mold (length, taper and the like) does not meet the alloy.

As shown in the pattern 5, in case the gradient is larger at the edge and smaller inside the ingot, it can be considered that the solidification pool was too deep, the primary cooling was good but the secondary cooling was not good or the casting speed was too fast.

Thus, the following information can be obtained from conductivity distribution pattern on the surface or the cross section of the ingot:

(1) Information on design such as material properties and the shape of the casting mold, the primary and the secondary cooling conditions, and the like.

(2) Information on presence or absence of dynamic or static distortion of the mold.

(3) Information on the properties of the surface of the mold (presence or absence of plating) and the behavior of flux.

(4) Information on segregation of the added element in the ingot.

(5) Information on the relationship between temperature of molten metal and occluded gas.

(6) Information on presence or absence of defect and crack, and the extent of residual stress in the ingot after casting.

Further sound alloy ingots can be obtained by establishing the melting and/or casting conditions based on above information. Furthermore, because this analytical method using conductivity does not require a complicated sample preparation unlike the analytical method according to the prior art, time required for analysis is shorter than that for the prior art. Therefore, analysis and simulation of material properties can be completed before the alloy ingot is forwarded to various steps after casting so that an ingot potentially creating poor quality can be removed before processing. Thereby, productivity can be improved and manufacturing cost can be reduced. Also, aforementioned information can be used for designing of better mold.

Further, the present invention can be applied to other precipitation hardening alloy such as Cu alloy, Al alloy, Fe alloy and the like in addition to said Cu-Fe alloy.

Furthermore, the present invention can be applied to other solid solution type alloy rather than precipitation hardening alloy if any element capable of changing its solid soluble limitation according to change of temperature is added as a marker in order to obtain the optimum melting and/or casting conditions according to the composition and the like of the alloy.

Figure 2:
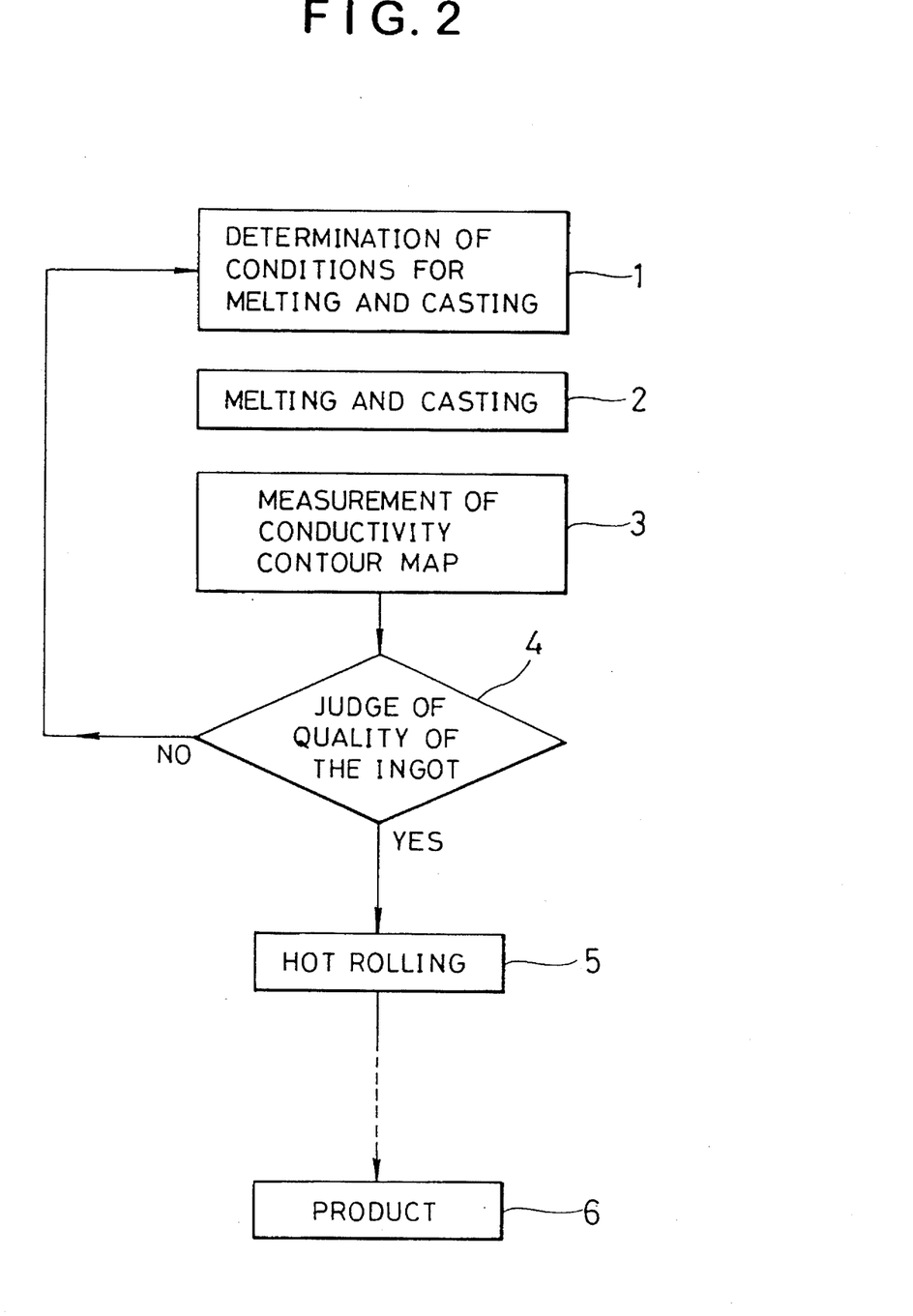
FIG. 2 is a flow chart of the manufacturing method of metal or alloy according to one embodiment of the present invention.

One embodiment of the present invention will be explained in detail referring attached drawings as follows. FIG. 2 is a flow chart showing a manufacturing method of metal or alloy according to one embodiment of the present invention. First in the step 1, considering manufacturing conditions such as a kind of metal or alloy to be casted, shape of casted product, conditions of manufacturing apparatus and the like, conditions for melting and casting are determined based on accumulated technical skill.

Next in the step 2, melting and casting of metal or alloy are actually carried out according to the conditions determined in the step 1 to obtain the ingots. Casting is carried out according to the continuous or semi-continuous casting method commonly being used for the commercial production of metal material, for example.

Then in the step 3, conductivity of the ingot is measured and conductivity contour map is prepared based on the results obtained. The measurement of conductivity is performed according to the following method, for example. Firstly, for measurement surface such as the surface or the cross section of the ingot, conductivity is measured automatically by moving the measuring sensor of the eddy current type conductivity meter in parallel to the surface of the sample at constant speed. Resolution and measurement speed can be changed by changing of the diameter of the tip of the measuring sensor, the intake cycle of signal from the measuring sensor and/or the moving speed of the measuring sensor. Where using the measuring sensor having the tip diameter of 5 mm, the intake cycle of the signal is set at 40 time/sec. and the moving speed of the measuring sensor at 100 mm/sec., conductivity can be measured at the rate of 50 mm$^2$/sec. with resolution of 2.5 mm. In addition to the aforementioned method, conductivity can be measured also using other methods; that is, a method in which the sensor is allowed to move upward and downward at constant cycle and to travel at the pre-determined distance during its upward movement while allow it contact with the sample during its downward movement or a method in which a disk placed with multiple measuring sensors on the peripheral thereof is allowed to rotate on the surface of the sample to be measured so as each sensor sequentially contacts with the sample. In either cases, signals from the measuring sensor are input to EWS, personal computer and the like and processed so as to link each point having the same conductivity with a curved line. Thereby, exact distribution of conductivity can be shown. Further, three-dimensional conductivity contour map can be shown, if necessary, by measuring conductivity of the sample at the equidistance toward the center after exposure of the new surface by grinding at arbitrary depth.

Further, the measuring sensor of the aforementioned eddy current type conductivity meter can be applied to the measurement of conductivity of paramagnetic materials. Then in the step 4, quality of the ingot is judged based on said conductivity contour map. In detail, for example, a pattern as shown in FIG. 1 is prepared in advance as the standard pattern and compared with a contour map pattern obtained from the sample to judge the quality of the ingot. If the contour map pattern obtained from the measurement is similar to the pattern 1 shown in FIG. 1, it can be judged that the quality of the ingot is acceptable. In this case, the process is proceeded to the step 5 to carry out the hot rolling, then to the step 6 through various processes to make the finished product. While the contour map pattern obtained from the measurement is similar to either pattern from 2 to 5, either or both melting and casting conditions are re-established according to the pattern obtained.

According to the present invention, quality of ingots can be assessed based on the conductivity distribution pattern of metal or alloy and melting and/or casting conditions are re-established based on the results obtained as aforementioned so that very healthy metal or alloy ingots can be manufactured. Further, according to the present invention because only measurement of conductivity on the outer surface or the cross section is used, quality of metal or alloy can be assessed very easy and quickly compared to any methods of prior art in which quality of ingots is assessed by various testings such as the tensile test, the impact test, the defect tests and the like, and the results obtained can be quickly reflected to melting and/or casting conditions. Furthermore, according to the present invention because residual stress, solid solution status of added element and the like can be grasped in two-dimensional or three-dimensional way, the results of quality assessment of ingots can be reflected to the following steps of casting. Since an ingot having locally high residual stress may easily create cracks during the rolling process, removing such ingot in advance results in improvement of productivity and consequently in reduction of manufacturing cost.

Figure 3:
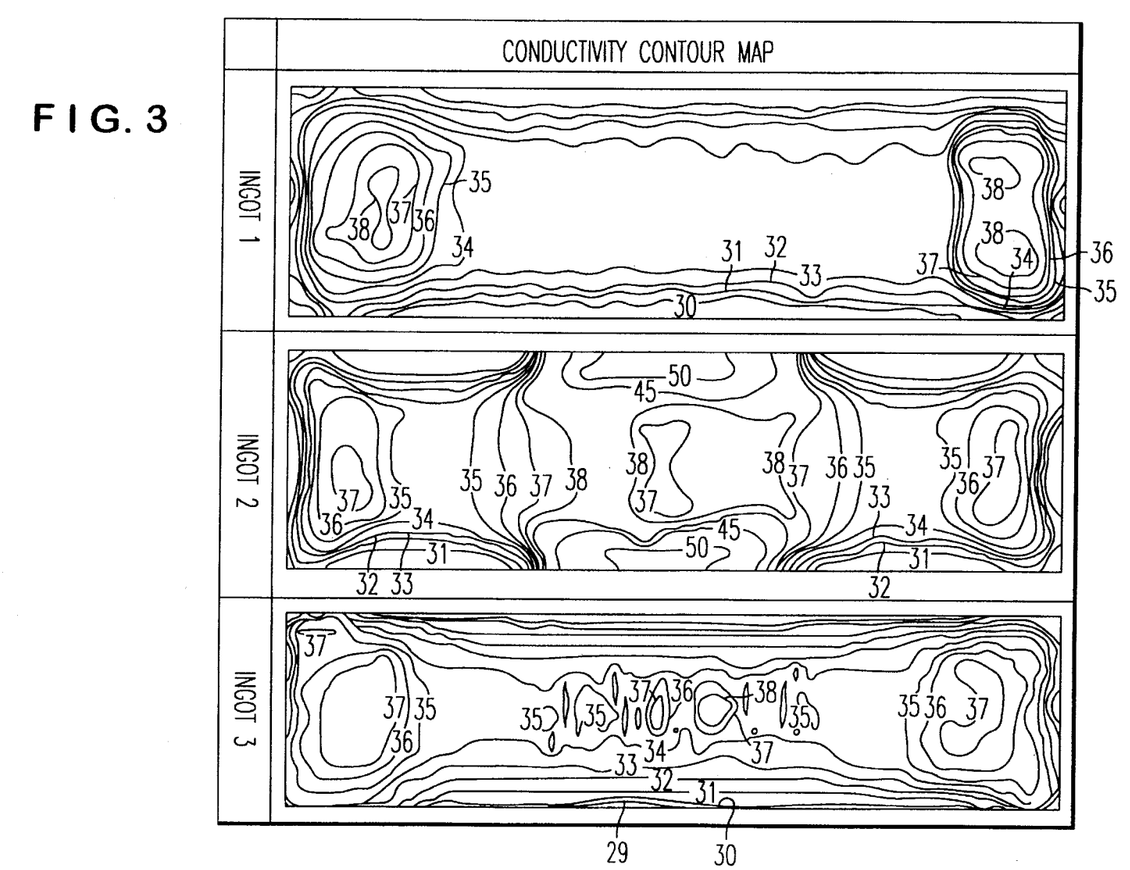
FIG. 3 is a conductivity contour map obtained from the manufacturing method of metal or alloy according to the same embodiment of the present invention.

Then, some examples of this embodiment applied to the manufacturing of copper alloy will be explained. Cu-2.3 wt. % Fe-0.03 wt. % P alloy of eight tons was melted using a high frequency furnace, then ingots, each 160 mm in thickness, 650 mm in width and 4 m in length, were prepared by the semi-continuous casting. After confirmed that macro- and micro-structure of both bottom and top of the ingot were in normal state, a sectioned sample of 30 mm in thickness was collected each from bottom and top of each ingot. Then, conductivity on the surface of these sectioned samples was measured using an eddy current type conductivity meter. Conductivity contour maps of the surface of these ingots are shown in FIG. 3. Based on these conductivity contour maps, melting and casting status and their conditions of metal or alloy was estimated, and characteristics of rolling and rolled materials were predicted. Results of these estimation and prediction are presented in Table 1 below.

Further, after the same ingots shown in FIG. 3 were heat rolled at 950° C. into 15 mm of thickness, rolled materials having thickness of 0.25 mm were prepared by performing the cold rolling and annealing. Material characteristics were measured after each step. Results are also presented in Table 1.

TABLE 1

| | Estimated melting and casting status and judgement of conditions | Predicted rolling and rolled material characteristics | Rolled material characteristics | |
|---|---|---|---|---|
| | | | Tensile strength kgf/mm$^2$ | Conductivity % IACS |
| Ingot 1 | Diverse cooling of mold. Insufficient cooling water at both sides of mold. High residual stress at both sides having larger gradient of conductivity. | Crack is predicted to occur at both sides during hot rolling. Area having low conductivity and sufficient annealing is good in aging treatment affect. | 56.4 | 72.9 |
| Ingot 2 | Insufficient cooling water over whole mold. High conductivity and poor solid solubility. | Insufficiency of strength of aged material is predicted due to poor solid | 49.8 (At area having high conductivity) 50.8 | 69.6 64.9 |

TABLE 1-continued

| | Estimated melting and casting status and judgement of conditions | Predicted rolling and rolled material characteristics | Rolled material characteristics | |
|---|---|---|---|---|
| | | | Tensile strength kgf/mm² | Conductivity % IACS |
| | Deformation in the middle of mold prevented uniform contact with ingot shell and created reduction of cooling efficiency. | solubility. | (At middle of mold) | |
| Ingot 3 | Diverse cooling of ingot due to deformation of mold and crack occurred during casting. | Unacceptable for hot rolling. | | |

As obvious from Table 1, for the ingot 2 judged to be poor in solid solubility, the tensile strength of rolled material was 49.8 or 50.8 kgf/mm² which was lower than 56.4 kgf/mm² of the tensile strength for rolled material from the ingot 1 and it confirmed that predicted characteristics of rolled material was correct.

Further, the ingot 3 was impossible to further process due to occurrence of crack and both ingots 1 and 2 were acceptable for partial or limited use. Thus, according to the present invention, there provided effects that based on measurement of conductivity on the cross section and characteristics of conductivity contour map pattern of the ingot the optimum melting and casting conditions can be determined and in addition to that quality of ingot and material characteristics after processing can be quickly predicted.

Then, a conductivity measuring apparatus capable of being used for measurement of conductivity in the method according to the embodiment of the present invention will be explained.

Figure 4:
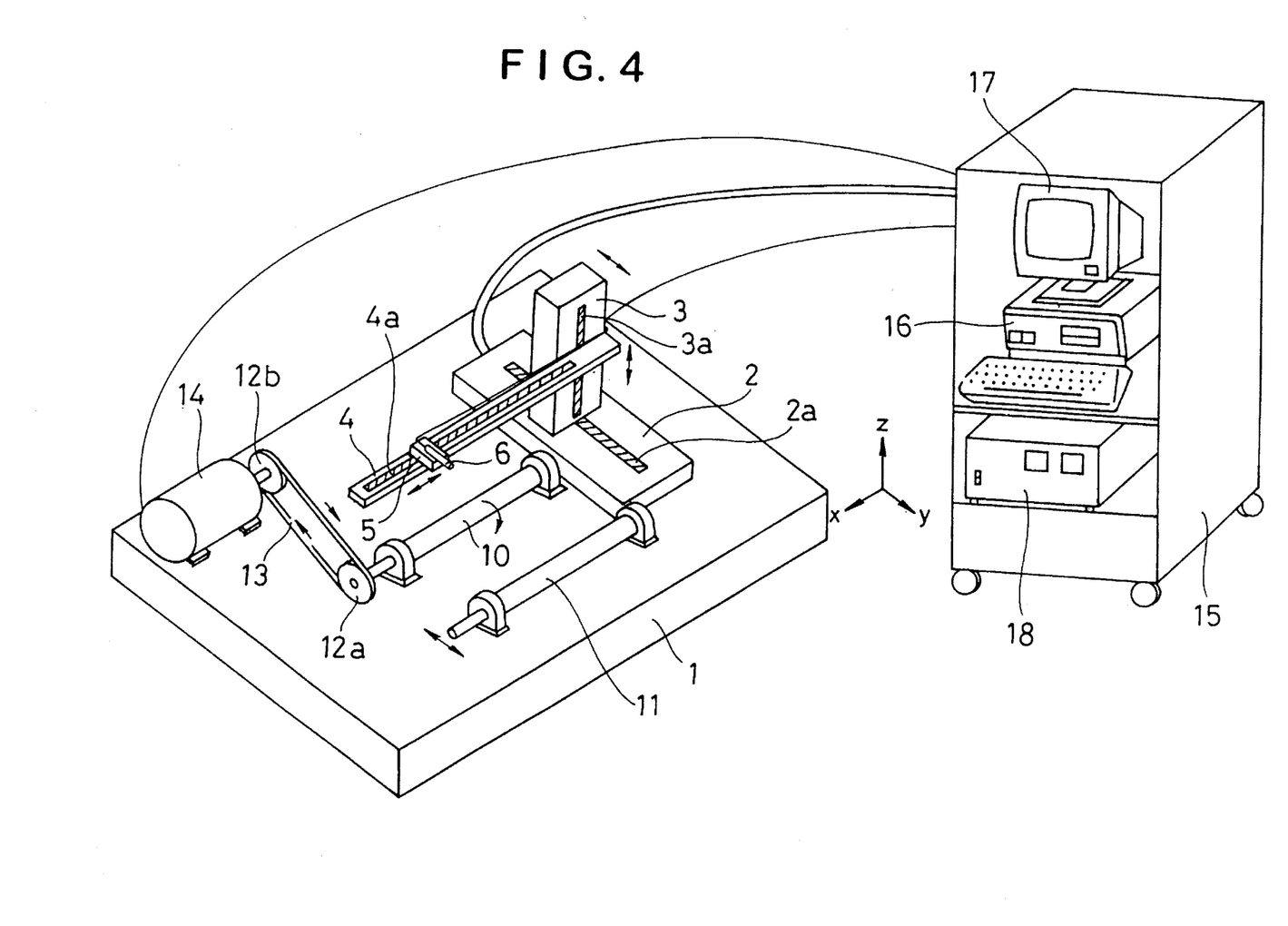
FIG. 4 is a perspective view showing an apparatus according to the embodiment of the present invention.
Figure 5:
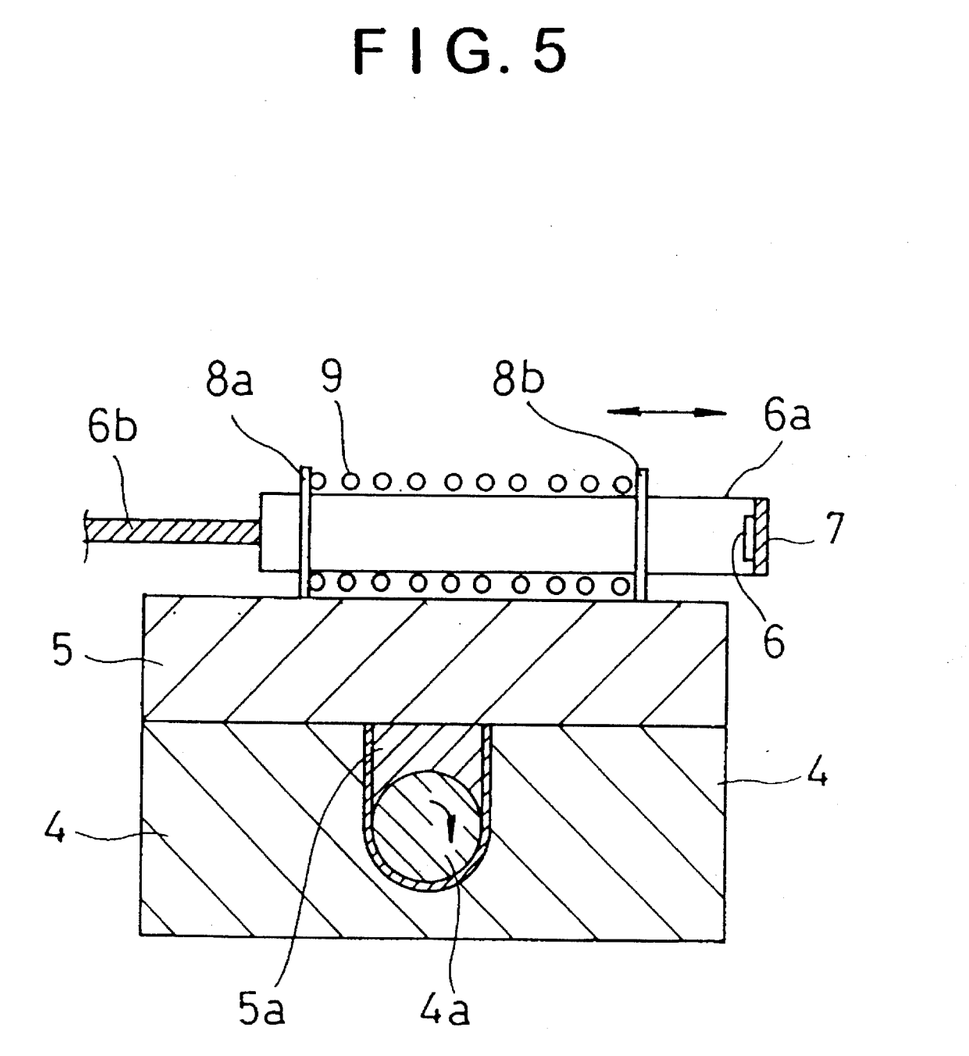
FIG. 5 is an enlarged sectional view showing a sensor part of the same.

FIG. 4 is a perspective view showing this conductivity measuring apparatus and FIG. 5 is a partially enlarged sectional view of the area near a conductivity measuring sensor of the same. On a table 1, a first arm 2 extending toward one direction (toward the direction of y-axis in the embodiment shown in FIG. 4) is fixed. In this arm 2, a screw rod 2a also extending toward the direction of y-axis is placed in a concave part provided in the arm 2 so as to allow this screw rod 2a reciprocally rotated around its axis by an appropriate driving means.

On the arm 2, an arm 3 extending vertically is placed so as to move toward the direction of y-axis against the arm 2. This arm 3 is engaged with the screw rod 2a at the bottom thereof so as to be moved by rotating screw rod 2a toward the direction of its axis, that is, y-axis by the similar mechanism as for a sensor described later.

In the arm 3, a concave part extending vertically is provided on side surface thereof and a screw rod 3a extending vertically is provided in this concave. This screw rod 3a is also rotated around its axis by an appropriate driving means.

To this arm 3, an arm 4 extending horizontally is placed so as to move toward vertical direction against the arm 3, that is, toward the direction of z-axis. This arm 4 is engaged with the screw rod 3a at one edge thereof so as to be moved by rotating screw rod 3a toward the direction of its axis, that is, z-axis by the similar mechanism as for a sensor described later.

In the arm 4, a concave extending toward the direction vertical against the screw rods 2a and 3a, that is, extending toward the direction of x-axis, and a screw rod 4a extending toward the direction of x-axis is provided in this concave.

This screw rod 4a is also rotated reciprocally by an appropriate driving means. Further, on this arm 4 a sensor holder 5 is provided so as to move toward the direction of the axis of the screw rod 4a against the arm 4, that is, toward the direction of x-axis as shown in FIG. 5. To this sensor holder 5 an engaging part 5a engaging with the screw rod 4a is provided at the bottom thereof and the screw rod 4a is engaged with this engaging part 5a. Thereby, when the screw rod 4a is rotated clock-wise or anti-crock-wise, the sensor holder 5 moves forward or backward the direction of x-axis through the engaging part 5a engaging with the screw rod 4a.

Further, up and down movement of the arm 4 and reciprocal movement of the arm 3 toward y-axis are also driven in similar manner by respective reciprocal rotation of the screw rod 3a and the screw rod 2a as aforementioned. Rotation of these screw rods 2a, 3a and 4a is driven by a pulse motor and each rotation rate can be highly controlled.

A conductivity measuring sensor 6 is placed on the tip of a cylindrical holding rod 6a which is supported by an appropriate supporting part (not shown) so as to move on the sensor holder 5 toward the direction crossing the screw rod 4a, that is, toward the direction of y-axis. Further, this holding rod 6a is inserted into a flange 8a fixed on the sensor holder 5 at the rear end thereof and fixed with a flange 8b at the front part thereof. Between both flanges 8a and 8b, a pressing spring 9 is provided so as to elastically press the sensor 6 toward the front end of the holding rod 6a. Therefore, since the sensor 6 is pressed onto the sample to be measured such as an ingot and the like by the elastic force of the spring 9, the sensor 6 continuously contacts with the sample to be measured through a liner 7 described later so as to keep a constant distance between the surface of the sample to be measured. The distance between the sensor 6 and the sample to be measured also can be maintained at constant by controlling the distance using a laser range finder. A lead 6b connected to the sensor 6 protrudes from the rear end of the holding rod 6a toward outside and is connected to a conductivity meter 18 described later.

Specifications of this conductivity measuring sensor 6 and the conductivity meter 18 are listed in Table 2 below as example. This conductivity measuring sensor 6 is capable of measuring the conductivity of a sample by generating an eddy current on the surface of the sample to be measured and then measuring the magnetic force by the eddy current. Therefore, it is not necessary to place the sensor 6 so as to directly contact with the surface of the sample. Accurate measurements can be obtained even if measurement carried out at distance about 0.5 mm apart from the surface of the sample, for example.

TABLE 2

| Item | Capacity |
| --- | --- |
| Range of measurement | 0.5–103% IACS |
| Accuracy of measurement | Measured value ± 1% |
| Resolution | 0.1% IACS |
| Measurement frequency | 60–480 kHz |
| Measurement temperature | 0–40° C. |
| Measuring cycle of conductivity (input cycle of signal) | 1/sec.–100/sec. |

To the tip of the conductivity measuring sensor 6 a liner 7 of silicon resin in 0.2 mm thick, for example, is attached so as to protect the sensor 6 from damage by friction with an ingot to be measured. This liner 7 may be comprised of not only silicon resin also any materials without conductivity and magnetic property such as other resins and ceramics and the like.

Further, the structure allows to use various conductivity measuring sensor with different diameter at the tip thereof. That is, the conductivity measuring sensors having different diameter are prepared in advance and a conductivity measuring sensor having suitable diameter is selected according to the diameter of the sample to be measured.

On the table 1, a pair of steel rollers 10 and 11 is provided in parallel with the arm 4 and the screw rod 4a. These rollers 10 and 11 are placed in parallel each other and at the same height. To one roller 10 a pulley 12a is attached at one end thereof. Both steel rollers 10 and 11 are covered with gum sheet so as to allow a measuring sample such as an ingot and the like placed on the rollers 10 and 11 to smoothly roll over the rollers 10 and 11 according to rolling thereof. The roller 10 and 11 may be comprised of not only steel also stain-less steel, resin, ceramics and the like.

Furthermore, on the table 1 a motor 14 is provided so as its driving shaft is in parallel with the roller 10, and a pulley 12b is fixed to this driving shaft. To these pulleys 12a and 12b are connected with a belt 13 so that the steel roller 10 is rotated by driving force of the motor 14. Thereby, an ingot to be measured is placed on the rollers 10 and 11 so as its axis is in parallel with rollers 10 and 11, then the roller 10 is rotated by the motor 14, so that the ingot is rotated around the center axis thereof. The motor 14 revolves at constant speed and thereby the ingot is also rotated at constant speed, but its rotation speed is determined by the measuring speed of the conductivity meter 18 and the diameter of the sample to be measured. Another roller 11 is placed on the table 1 so as its position against the table 1 can be adjusted to cross the direction of the axis of both rollers 10 and 11, that is, to the direction of y-axis. Thereby, the distance between the rollers 10 and 11 can be adjusted according to the diameter of the ingot to be measured.

In a movable box 15, a conductivity meter 18, a computer 16 and a CRT 17 are placed. This conductivity meter 18 is connected to the sensor 6 through the lead 6b and computes conductivity from the detection signals periodically received from the sensor 6. The conductivity meter 18 corrects the measured conductivity to the value at 20° C. The conductivity meter 18 transfers the calculated results of measured conductivity to a computer 16 through an interface. A step motor (not shown) driving the screw rods 2a, 3a and 4a inputs its revolution speed to the computer 16 which computes the position of the sensor 6 from these data. The peripheral speed and the dimension of the ingot to be measured are input to the computer 16 which controls the rotation speed of the motor 14 so as the pre-determined peripheral speed can be obtained. Thus, the computer 16 displays conductivity corresponding to the measured position calculated from measured conductivity for each measured position on the CRT 17.

The computer 16 can be constituted by a personal computer or a work station and displays conductivity distribution in the sample to be measured after processing of measured signals of the sensor 6 as contours or by color classification. For this display form, either development of the outer or inner faces of the ingot to be measured or three-dimensional graphics can be used.

Then, the operation of the conductivity measuring apparatus constructed as aforementioned will be explained. A cylindrical ingot (not shown) to be measured is placed on the rollers 10 and 11 so as to be held by both rollers 10 and 11 and its axis direction be in parallel with the rollers 10 and 11. The dimension and shape (either cylindrical or tubular) of the ingot, selection of the measuring surface (outer or inner) if the ingot is tubular, the length of measurement, the peripheral rotation speed of the ingot, the speed of the conductivity measuring sensor 6 moving toward the direction of the axis of the ingot are input to the computer 16 in dialog style, and then a measurement start button (not shown) is pressed. Thereby, the motor 14 rotates under control of the computer 16, the conductivity measuring sensor 6 moves to the measurement start position from the awaiting position and then moves toward the direction of x-axis to start measurement of conductivity. After measured conductivity for the pre-determined period, the conductivity measuring sensor 6 returns to the awaiting position.

The computer 16 retains the measured conductivity data together with corresponding measured position and computes data after completion of measurement in order to display conductivity by contour or color classification, and displays the computed results on the CRT 17. Further, the maximum and minimum values as well as individual values can be assigned by input of data thereof into the computer or can be automatically established by the computer. The measured results are displayed on the CRT 17 and also can be output to printer as well.

Thus, for the whole area of the outer surface of the cylindrical ingot, conductivity can be quickly measured.

In case a sample to be measured is tubular, the arm 4 and the sensor 6 can be inserted into the inside of tube so that conductivity distribution on the inner surface of the sample can be measured.

Then, actually measured results of conductivity distribution in an ingot using the conductivity measuring apparatus aforementioned will be explained.

Example 1

Billets, 300 mm in diameter and 5000 mm in length, were prepared by the semi-continuous casting of phosphorous deoxidized copper (Cu; 0.03 wt. % of P). A sample, 500 mm in length, was collected by cutting out from the bulk part of this billet and measured for conductivity. Before measurement, a sample, 150 mm in radius curvature, was cut out from copper and copper alloy C10100 (102% IACS), C26000 (28% IACS), C52100 (13% IACS) and aluminum alloy A1050 (61% IACS) with uniform composition and macro- and micro- structures after the working and heat treatment and used in calibrations of the conductivity measuring sensor and the conductivity meter.

Both atmospheric and sample temperatures were 30° C. at measurement. A conductivity measuring sensor with the diameter of 5 mm was used, the rotation speed of the sample as determined by the peripheral speed was 100 mm/sec., the sensor movement speed toward x-axis was 0.5 mm/sec., and the measurement period was 1000 sec.

Figure 6:
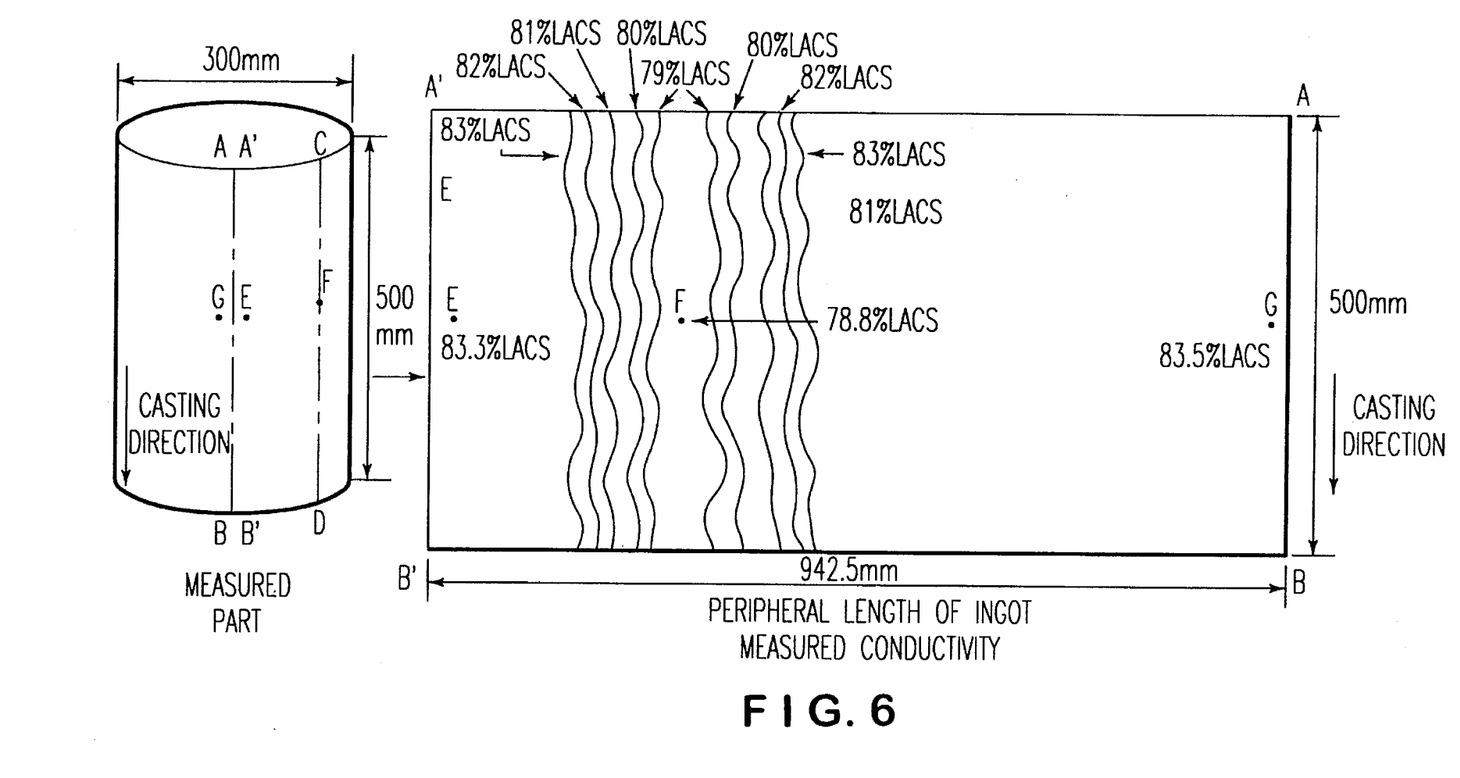
FIG. 6 is a contour map showing conductivity distribution of the example 1.

FIG. 6 is the measured conductivity distribution shown by contour.

There can be seen a strip with lower conductivity extending toward the direction of casting, indicating that phosphorous concentration is higher in this area because conductivity correlates approximately with solid solution amount of phosphorous within the range of phosphorous concentration from 0 to 0.1%. It is considered that deformation of the mold prohibited heat release in this area where phosphorous rich molten metal exuded. Dimension of the mold was determined and deformation of the mold was found at the position 15 mm deeper from the meniscus which corresponds to the exuded position.

Example 2

Billets, 200 mm in diameter and 3500 mm in length, were prepared by the semi-continuous casting of A6063-alloy (Al- 0.7 wt. % Mg-0.4 wt. % Si).

A sample, 400 mm in length, was collected by cutting out from the bulk part of this billet and measured for conductivity. Before measurement, a sample, 100 mm in radius curvature, was cut out from copper and copper alloy C10100 (102% IACS), C26000 (28% IACS), C52100 (13% IACS) and aluminum alloy A1050 (61% IACS) with uniform composition and structures after the working and heat treatment and used in calibrations of the conductivity measuring sensor and the conductivity meter.

Both atmospheric and sample temperatures were 25° C. at measurement. A conductivity measuring sensor with the diameter of 5 mm was used, the rotation speed of the sample as determined by the peripheral speed was 100 mm/sec., the sensor movement speed toward x-axis was 0.8 mm/sec., and the measurement period was 500 sec.

Figure 7:
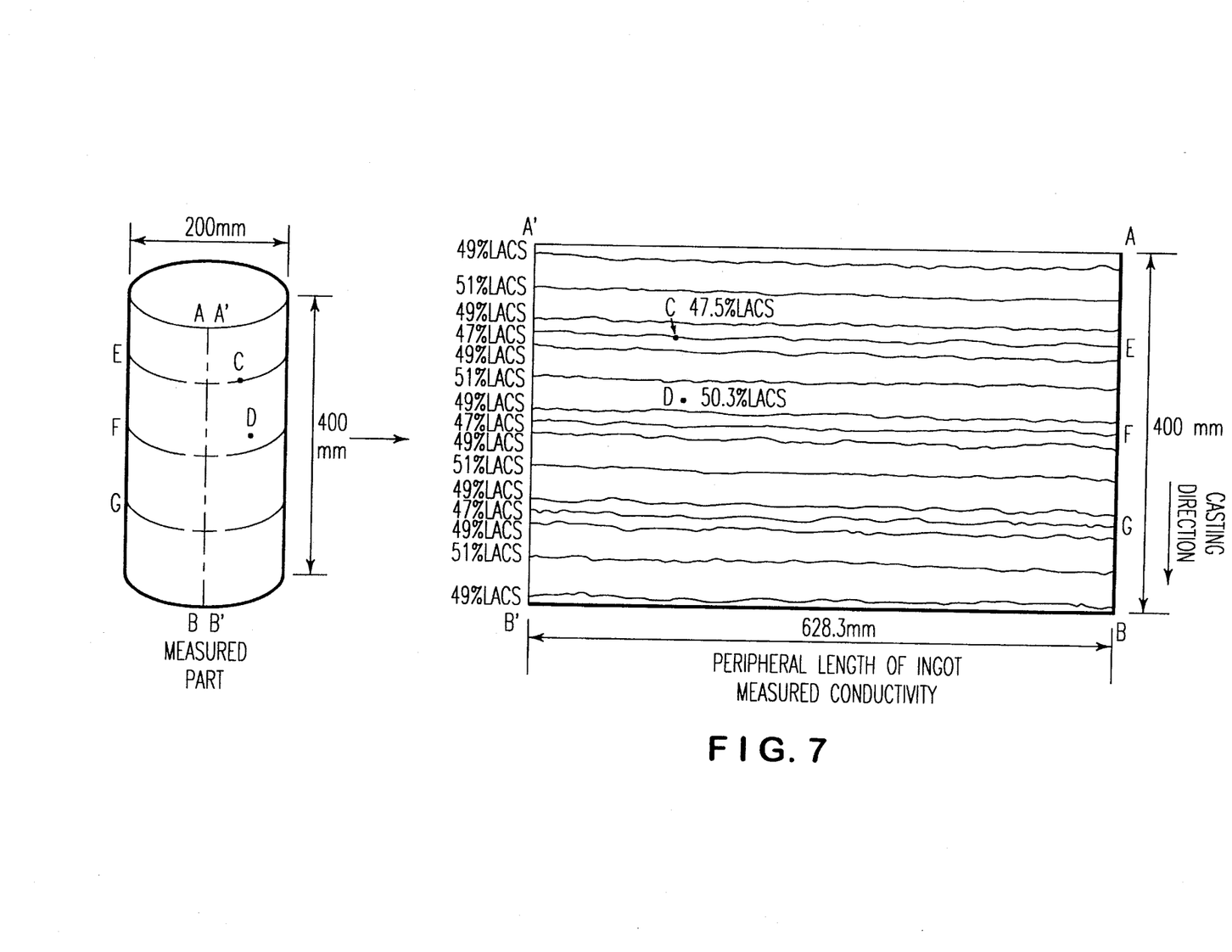
FIG. 7 is a contour map showing conductivity distribution of the example 2.

FIG. 7 is the measured conductivity distribution shown by contour. The maximum conductivity was 51% IACS, the minimum conductivity was 47% IACS, and the maximum and the minimum vales appeared at about 50 mm cycle. It was considered that the area having lower conductivity corresponded to the exuded position.

Observation of macro- and micro-structures of ingot supported the above findings, indicating that the thickness of the solidification shell shows cyclic changes, particularly in the area having lower conductivity the shell was thin and concentrations of Mg and Si were higher due to exudation. Based on these results, the cone angle of the mold was increased so as the diameter of upper part of the mold is larger than that of lower part of the mold, then casting was repeated again with higher casting speed. As a result, the exudation was decreased significantly.

According to the conductivity measuring apparatus of the present invention for paramagnetic materials, conductivity distribution on the outer or inner surfaces of cylindrical or tubular paramagnetic metal materials can be quickly and accurately measured. Thus, properties of continuously casted materials, semi-continuously casted materials, molded materials, extruded materials, rolled materials and heat treated materials of paramagnetic metal or alloy such as Cu/Cu alloy, Al/Al alloy, Mg/Mg alloy, non-magnetic steel, stain-less steel, Ti/Ti alloy, Ni/Ni alloy, Co/Co alloy, Au/Au alloy, Zn/Zn alloy, Sn/Sn alloy, Pb/Pb alloy, Zr/Zr alloy, Ta/Ta alloy, Mb/Nb alloy, Mo/Mo alloy, W/W alloy and the like, further composite materials of said metal or alloy base containing metal fiber or particles, ceramic fiber or particles and the like, as well as paramagnetic materials such as clad materials of said metal or alloy and the like can be quickly confirmed at site of production, so that the present invention offers a great contribution in assessment of suitability of conditions for casting, extrusion and heat treatment and in selection of raw materials and the like. Therefore, according to the present invention, significant effects such as improvements in quality, productivity and yield can be obtained at production site of these materials.

Figure 8:
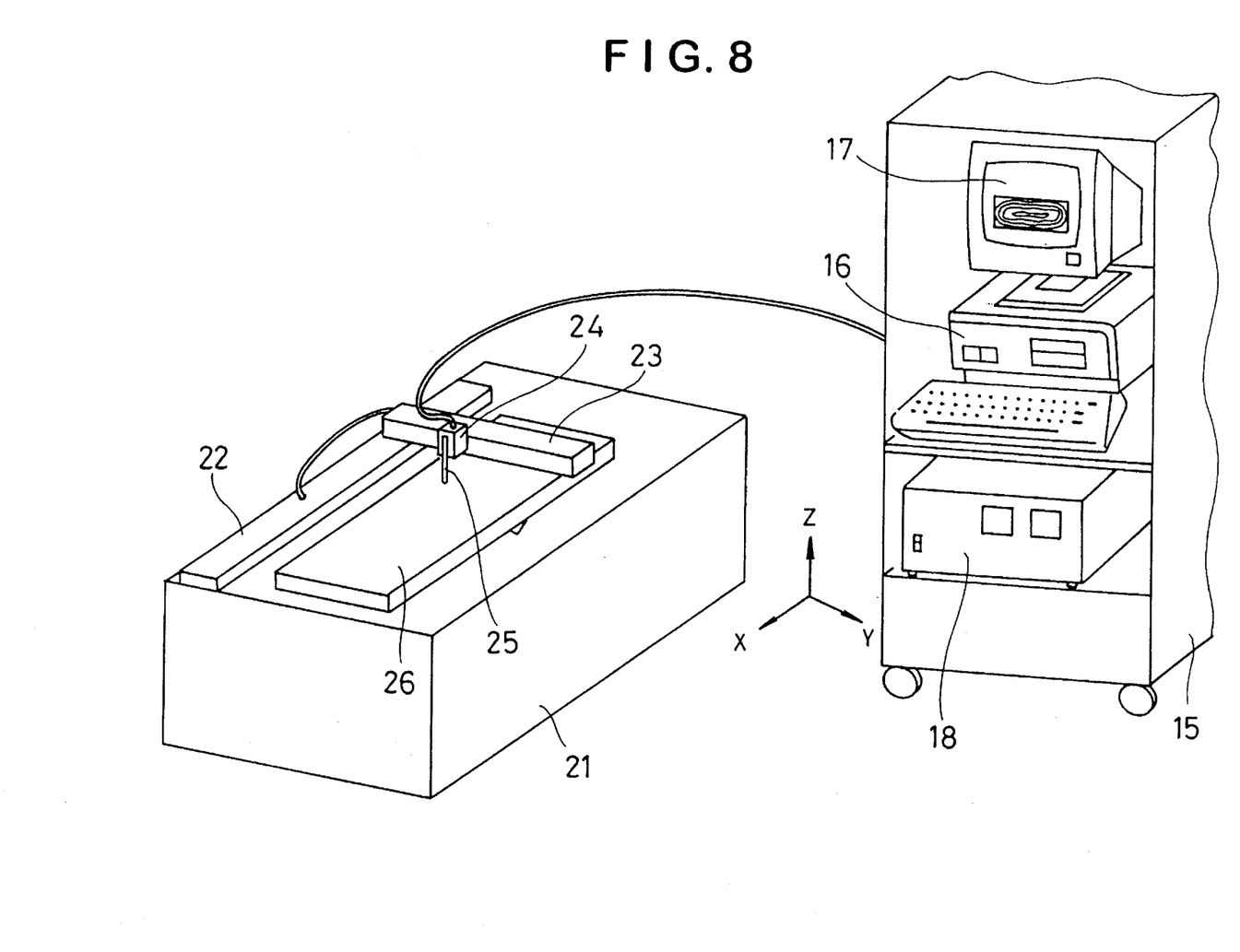
FIG. 8 is a perspective view showing an apparatus according to another embodiment of the present invention.

FIG. 8 is a diagram showing another conductivity measuring apparatus. On a table 21, a X-axis arm 22 and a Y-axis arm 23 are provided. The X-axis arm 22 is fixed on the surface of the table 21, and the Y-axis arm 23 is placed vertically on the X-axis arm 22 so as to move toward the longitudinal direction of the X-axis arm 22, that is, toward the direction of the X-axis. Further, to the Y-axis arm 23, a Z-axis arm 24 is placed so as to move along the Y-axis arm 23. Furthermore, to the Z-axis arm 24 a sensor 25 is attached so as to move toward the vertical direction against the surface of the table 21, that is, toward the direction of Z-axis. The output of this sensor 25 is connected to a conductivity meter 18, and the conductivity meter 18 computes conductivity based on the output of the sensor 25 and outputs the results to a computer 16, then displays conductivity distribution on a CRT 17. The computing process of this computer 16 is the same as the computing method for the apparatus shown in FIG. 4.

The apparatus shown in FIG. 8 is characterized in that the sensor 25 moves toward the directions of X-Y and measures conductivity on X-Y surface of an ingot. That is, the apparatus measures conductivity distribution of a plate type ingot 26. Thus, according to the present invention, the plate type ingot 26 is placed on the table 21, then the attached position of the sensor 25 against the Z-axis arm 24 is adjusted so that the height thereof, that is, the distance between the detection tip of the sensor 25 and the surface of the ingot 26 is adjusted. Then, this sensor 25 and the Z-axis arm 24 are moved toward the directions of X-axis and Y-axis along the X-axis arm 22 and the Y-axis arm 23, and conductivity distribution on X- and Y-axis surfaces of the ingot 26 is measured.

Further, the position of the sensor 25 at the direction of Z-axis, that is, the height of the sensor can be adjusted at the central position of the ingot 26 after initiation of measurement by moving first the sensor 25 to the center of the ingot 26. Measurements of conductivity determined by the sensor 25 are corrected to conductivity at 20° C. by the conductivity meter 18.

Then, results of conductivity distribution actually measured using the apparatus shown in FIG. 8 will be explained.

Example 3

Cu-2.3 wt. % Fe-0.03 Wt. % P alloy (8 tons) was melted using a high frequency furnace, and ingots, 160 mm in thickness, 650 mm in width and 5000 mm in length, were prepared by the semi-continuous casting. A sectional sample, 50 mm in thickness, was collected by cutting out at the 500 mm from the bottom where metal tissue and heat transfer coefficient are stable, and milling of cut surface was made. Before measurement, a sample, 10 mm in thickness, was cut out from copper and copper alloy C10100 (102% IACS), C26000 (28% IACS), C52100 (13% IACS) and aluminum alloy A1050 (61% IACS) with uniform composition and structure after the working and heat treatment and used in calibration of the conductivity measuring sensor and the conductivity meter.

The movement speed of the sensor 25 toward the direction of Y-axis 100 mm/sec. and the movement pitch toward the X-axis 5 mm were input to the computer 16, and conductivity distribution on the sectional sample was measured. The measurement period was 130 sec. and both atmospheric and sample temperatures were 30° C. at measurement.

Figure 9:
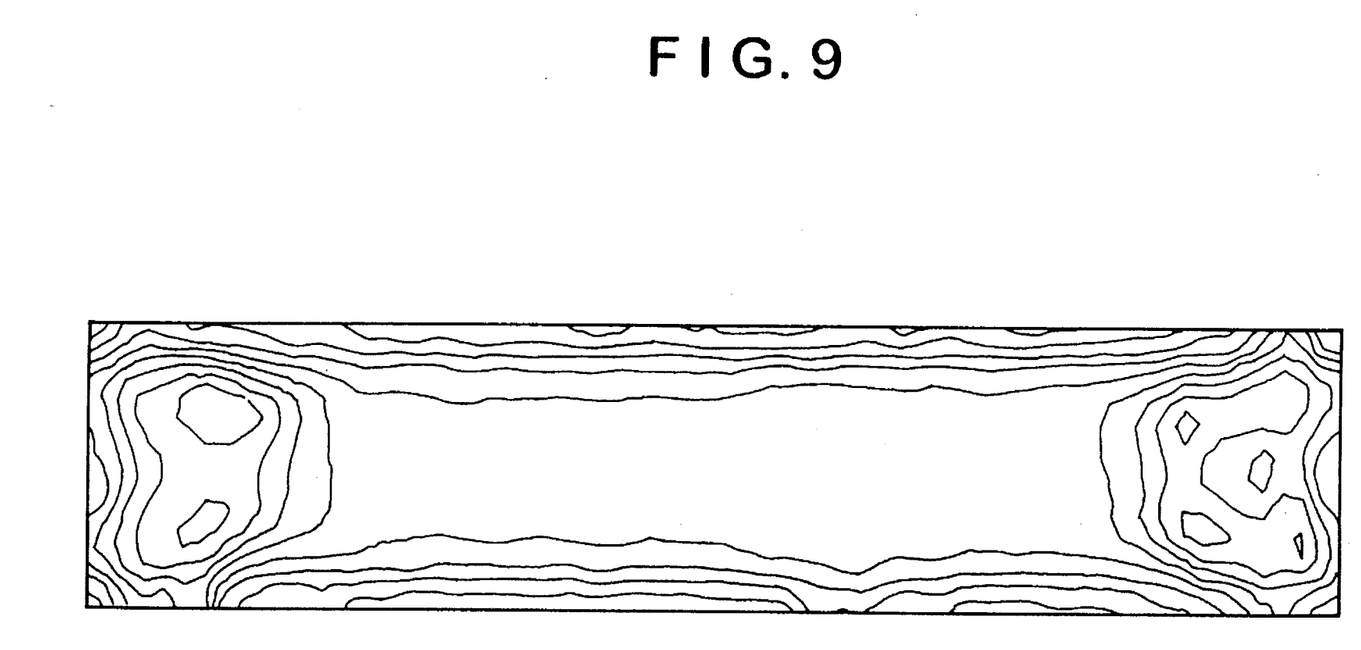
FIG. 9 is a contour map showing conductivity distribution of the example 3.

Conductivity distribution contour map obtained is shown in FIG. 9. The minimum conductivity was 27.5% IACS, the maximum conductivity was 36.8% IACS, and the looped area having the maximum value appeared in the area 70 to 80 mm inner from the shorter edge. Therefore, it was predicted that the primary cooling at the side of the shorter edge during the casting was weaker than that at the side of longer edge.

Example 4

Billets, 300 mm in diameter and 5000 mm in length, were prepared by the semi-continuous casting of phosphorous deoxidized copper (Cu; 0.03 wt. % P). A sectioned sample was collected by cutting out from the steady part of this billet and measured for conductivity. Similar to Example 3, calibrations of the conductivity measuring sensor 25 and the conductivity meter 18 were performed.

The movement speed of the sensor 25 toward the direction of Y-axis 100 mm/sec. and the movement pitch toward the X-axis 5 mm were input to the computer 16, and conductivity distribution on the cross section was measured. The measurement period was 180 sec. and both atmospheric and sample temperatures were 25° C. at measurement.

Conductivity distribution classified by color indicated that the minimum conductivity was 82.5% IACS in the surface part, the maximum conductivity was 85% IACS in the middle part about 80 mm inner from the surface, and areas having equal conductivity were distributed as rings. Therefore, it was found that heat release by the primary and the secondary cooling was uniform over the whole ingot.

What is claimed is:

1. A manufacturing method of metal or alloy comprising the steps of:

melting and casting raw materials under certain melting and casting conditions to produce a casting material;

obtaining a conductivity distribution pattern by measuring of conductivity on one of the surface and cross section of the casting material; and re-establishing melting and casting conditions of raw materials based on data from the conductivity distribution pattern.

2. A manufacturing method of metal or alloy comprising the steps of:

obtaining molten metal by melting raw materials;

casting the molten to obtain an ingot;

measuring conductivity on the surface or the cross section of the ingot to obtain a conductivity distribution pattern;

establishing melting conditions of said raw materials and casting conditions of said ingot based on data from the conductivity distribution pattern; and melting and casting based on said melting conditions and casting conditions.

3. A manufacturing method of metal or alloy according to claim 1 or 2, wherein said alloy is comprised of paramagnetic metal or alloy.

4. A manufacturing method of metal or alloy according to claim 3, wherein said alloy is comprised of precipitation hardening metal or alloy.

5. A manufacturing method of metal or alloy according to claim 3, wherein said alloy is comprised of copper or copper alloy.

6. A manufacturing method of metal or alloy according to claim 3, wherein said alloy is comprised of aluminum or aluminum alloy.

* * * * *